United States Patent [19]

Diamond et al.

[11] Patent Number: 4,517,310

[45] Date of Patent: May 14, 1985

[54] N-[2-HYDROXY-2-(3-HYDROXYPHENYL)E-THYL]-1H-BENZIMIDAZOLE-1-BUTANA-MINE AND USE THEREOF AS A CARDIOTONIC AGENT

[75] Inventors: Julius Diamond, Mountain Lakes; Ronald A. Wohl, Morris Plains, both of N.J.

[73] Assignee: Berlex Laboratories, Inc., Cedar Knolls, N.J.

[21] Appl. No.: 287,605

[22] Filed: Jul. 28, 1981

[51] Int. Cl.$^3$ .................. A61K 31/415; C07D 235/06
[52] U.S. Cl. ..................................... 514/394; 548/333
[58] Field of Search ...................... 548/333; 424/273 B

[56] References Cited

U.S. PATENT DOCUMENTS 3,905,990 9/1975 Ehrmann et al. ................... 548/333

FOREIGN PATENT DOCUMENTS 2833140 2/1980 Fed. Rep. of Germany ...... 548/333

OTHER PUBLICATIONS

Evans, D., et al., Pharmac. Ther. 16, 303 (1982).
Sonnenblick, E., et al., New Eng. J. Med., 300 (1), 17 (1979).

Primary Examiner—Richard A. Schwartz
Attorney, Agent, or Firm—Elizabeth A. Bellamy; John L. White; I. William Millen

[57] ABSTRACT

The compound N-[2-hydroxy-2-(3-hydroxyphenyl)ethyl]-1H-benzimidazole-1-butanamine and methods for its manufacture and use are described herein. The compound is a cardiotonic agent useful primarily in the treatment of congestive heart failure.

7 Claims, No Drawings

N-[2-HYDROXY-2-(3-HYDROXYPHENYL)ETHYL]-1H-BENZIMIDAZOLE-1-BUTANAMINE AND USE THEREOF AS A CARDIOTONIC AGENT

FIELD OF THE INVENTION

This invention relates to novel compositions of matter, to methods for their production, and to their use as cardiotonic agents. Specifically, this invention relates to N-[2-hydroxy-2-(3-hydroxyphenyl)ethyl]-1H-benzimidazole-1-butanamine and the pharmaceutically acceptable acid addition salts thereof, useful as cardiotonic agents primarily in the treatment of congestive heart failure. Further, this invention relates to pharmaceutical compositions comprising said compounds and to methods for their use in treating congestive heart failure.

GENERAL DESCRIPTION OF THE INVENTION COMPOSITION-OF-MATTER ASPECT

This invention relates to the compound of the following formula:

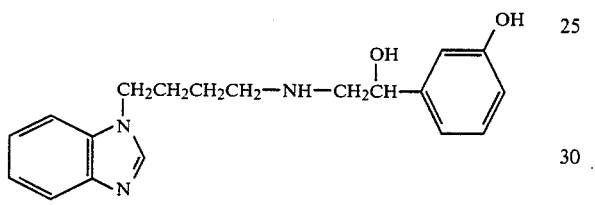

which is N-[2-hydroxy-2-(3-hydroxyphenyl)ethyl]-1H-benzimidazole-1-butanamine and to the pharmaceutically acceptable acid addition salts thereof. Such salts, prepared by methods well known in the art, are formed with both inorganic or organic acids, e.g. hydrochloric, hydrobromic, sulphuric, phosphoric, acetic, propionic, benzoic, naphthoic, oxalic, succinic, maleic, malic, adipic, lactic, tartaric, citric, salicylic, methanesulphonic and p-toluenesulphonic.

In the compound of this invention, the carbinol carbon of the 2-hydroxymethyl group is an asymmetric center, therefore one pair of optical isomers is possible. It is to be understood that the definition of our compound encompasses all possible stereoisomers and mixtures thereof, which possess the activity discussed herein. In particular, it encompasses both the racemic form and isolated optical isomers which possess the indicated activity. The individual optical isomers can be obtained from the racemate by standard procedures, such as forming a salt with an optically active acid followed by crystallization.

PROCESS ASPECT OF THE INVENTION

A variety of procedures are available for the preparation of the compound of this invention. The most convenient makes use of either the aminoalkyl compound of the formula:

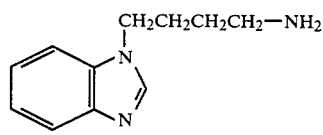

or the haloalkyl compound of the formula:

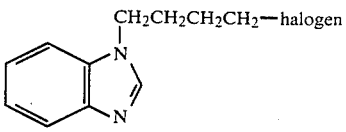

wherein halogen is preferably chorine or bromine.

When the amino compound is selected as a starting material, it can be reacted with any of the following three reagents:

a glyoxal of the formula:

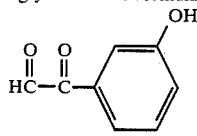

a bromoketone of the formula:

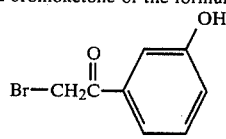

an oxirane of the formula:

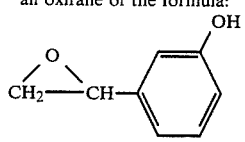

Alternatively, the phenolic hydroxy group can be in the form of a corresponding ether such as the benzyl ether or in the form of an ester such as the acetate ester. The ether or esters indicated serve as hydroxyl protecting groups which can be removed at a later stage in the process. The benzyl group is conveniently removed by treatment with hydrogen and palladium on charcoal while the methyl ether can be cleaved with reagents such as hydrogen bromide or boron tribromide. Esters can be removed by alkaline hydrolysis or other standard procedures for the elimination of such groups.

When the glyoxal is reacted with the amino alkyl compound, the product formed is the iminoketone of the formula:

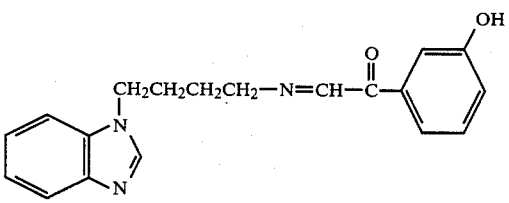

The reaction is preferably carried out in the presence of a dehydrating agent such as appropriate molecular sieves although the product can be obtained without the use of such a reagent. The iminoketone is reduced to the desired product using a reagent such as sodium borohydride. Any protecting group present on the hydroxyl moiety can be removed separately.

When a bromoketone or an oxirane is used, it may be desirable to use the aminoalkyl compound in the form of the corresponding N-benzyl derivative in order to avoid bis-alkylation of the amine or other undesired reactions. The N-benzyl group can be removed readily to give the desired compound. Actually, when the bromoketone is reacted with the N-benzylamine as indicated above, a ketone having the following formula is obtained:

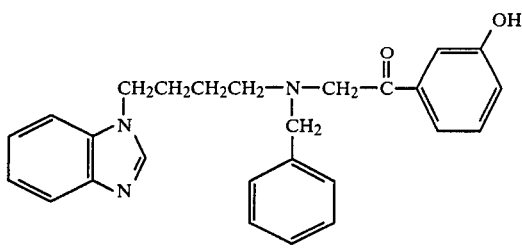

This intermediate can be converted to the desired compound by first reducing the ketone to the corresponding alcohol using a reducing agent such as sodium borohydride followed by removal of the protecting groups or the intermediate ketone can be treated with hydrogen and palladium on charcoal to effect simultaneous reduction of the ketone and removal of the benzyl group. In the case of the oxirane, the desired compound is obtained directly or after removal of N-benzyl and hydroxyl protecting groups if present.

When the haloalkyl compound is used as a starting material, it is reacted with an aminoalcohol of the formula:

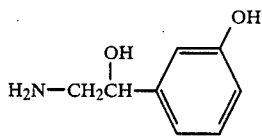

This reaction gives the desired product directly, or after removal of a phenolic hydroxy protecting group if present.

METHOD-OF-USE AND PHARMACEUTICAL COMPOSITION ASPECT

Surprisingly, the phenethylaminoalkylbenzimidazole, N-[2-hydroxy-2-(3-hydroxyphenyl)ethyl]-1H-benzimidazole-1-butanamine (compound F in the following table) is uniquely useful as a cardiotonic agent, primarily in the treatment of congestive heart failure. Heretofore, some of the known phenethylaminoalkylbenzimidazoles have exhibited usefulness as hypotensive agents, broncholytics and uterus relaxants. Their activity as hypotensive agents removes them from interest as cardiotonic agents.

For a pharmacologic agent to be considered as a cardiotonic agent useful primarily for the treatment of congestive heart failure (CHF), it must exhibit the following properties:

1. Strong positive inotropic effect, i.e., increased force of ventricular contraction.
2. Increased cardiac output (CO).
3. Increased stroke volume and stroke work.
4. Reduction in total peripheral resistance (TPR).
5. Blood pressure (BP) must be maintained in normal range to assure good perfusion of vital organs.
6. Minimal effect on heart rate (HR), to avoid exerting the ischemic heart.

The following table is illustrative of the hemodynamic profiles of a series of phenethylaminoalkylbenzimidazole acid addition salts, which were tested in the pentobarbital anesthetized dog and were administered i.v. The inotropic dose ($ID_{100}$) is the amount of the compound expressed in micrograms per kilogram, which had to be administered in order to increase the baseline force of ventricular contraction in the animal by 100%.

HEMODYNAMIC EFFECTS OF PHENETHYLAMINOALKYLBENZIMIDAZOLES IN THE PENTOBARBITAL ANESTHETIZED DOG AT THEIR I.V. INOTROPIC DOSE ($ID_{100}$)

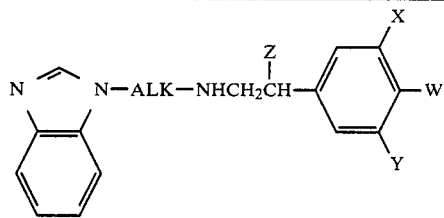

| COMP | ALK | Z | X | W | Y | INOTROPIC DOSE ($ID_{100}$) µg/kg i.v. | % ΔBP | % ΔHR | % ΔCO | % ΔTPR |
|---|---|---|---|---|---|---|---|---|---|---|
| A | —(CH₂)₃— | OH | H | H | H | | | | | |
| B | —(CH₂)₃— | H | OH | H | H | >400. | −25 | +8 | +20 | −40 |
| C | —(CH₂)₃— | OH | OH | H | H | 0.8 | −23 | +16 | +60 | −44 |
| D | —(CH₂)₃— | OH | OH | H | OH | 0.8 | −32 | +20 | +29 | −32 |
| E | —(CH₂)₃— | H | OH | H | OH | 12. | −16 | +18 | +36 | −37 |
| F | —(CH₂)₄— | OH | OH | H | H | 8. | −1 | +8 | +34 | −24 |
| G | —(CH₂)₅— | OH | OH | H | H | 180. | −17 | +11 | +38 | −36 |
| H | —(CH₂)₃— | OH | H | OH | H | 1.5 | −23 | +20 | +35 | −42 |
| I | —(CH₂)₄— | OH | H | OH | H | 8. | −13 | +12 | +30 | −32 |
| J | —(CH₂)₃CH(Me)— | OH | OH | H | H | 24. | −32 | +16 | +25 | −37 |
| K | —(CH₂)₂CH(Me)— | OH | OH | H | H | 0.3 | −18 | +25 | +40 | −40 |
| L | —(CH₂)₂CHMe— | H | OH | H | H | | | | | |
| M | —(CH₂)₂CMe₂— | OH | OH | H | H | 12000 | −30 | +20 | +55 | −55 |

As is amply illustrated by the data in the foregoing table only one compound, Compound F, the compound of this invention, as both its hydrochloride and oxalic acid salts exhibited the profile desired for a cardiotonic agent.

All of the compounds A-M showed positive inotropic activity, increased cardiac output and reduction in total peripheral resistance characteristic of β-adrenergic agonists. However, only compound F achieved these properties without affecting blood pressure and with minimal effect on heart rate.

Marked reduction in blood pressure is not desirable in a cardiotonic agent useful in the treatment of congestive heart failure because (1) it can result in the poor perfusion of vital organs, and (2) it can produce a reflex tachycardia (increased heart rate) which is detrimental to the near exhausted cardiac tissue of the failed heart.

Compound F also exhibited bronchodilator activity in the dog although this activity does not interfere in its application as a cardiotonic agent, one would not ordinarily use compound F as a bronchodilator, since it exerts a strong positive inotropic effect on the heart at bronchodilating doses.

The cardiotonic agent of this invention can be administered orally, compounded in the form of tablets, capsules, elixirs or the like. The compound may also be administered parenterally via intravenous or intramuscular injection.

The pharmaceutical carriers useful in the preparation of the foregoing formulations will include, for example, such substances as water, oils, fats, waxes, polyesters, alcohols, polyols and the like.

In general, the dosage administered of a compound of this invention will be dependent on the age and weight of the mammalian host being treated. Said host (preferably an adult human) having a disease state receptive to being treated by a cardiotonic agent, particularly the disease state CHF. The precise dose will depend on the stage and severity of the disease. For instance, for the treatment of CHF the total oral dosages can range from 20-80 mg b.i.d. to q.i.d., with 40 mg t.i.d. as probably the preferred dosage.

As an injectable, the compound of this invention would most generally be administered as a slow i.v. infusion at a dose of 4-16 mcg/kg/min. with about 8 mcg/kg/min. being the most preferred. The compound when administered by i.v. infusion is usually in the form of a salt such as the hydrochloride or hydrobromide. Preparations of the salt suitable for i.v. infusion are, for example, a 5% glucose solution containing a desirable clinical concentration of the compound in the salt form. Such a solution is desirably maintained at an acidic pH.

The invention described hereinabove is illustrated in detail hereinbelow in the Examples and Formulations which are not to be construed as limiting the scope of our invention.

EXAMPLE 1

N-[2-hydroxy-2-(3-hydroxyphenyl)ethyl]-1-H-benzimidazole-1-butanamine

A. Preparation of 1H-benzimidazole-1-butanenitrile

To a suspension of 23.6 grams of benzimidazole in 300 ml of dioxane is added 9.8 grams of a 50% dispersion of sodium hydride in mineral oil and the resulting mixture is stirred at room temperature for two hours. Then a solution of 20.7 grams of 4-chlorobutyronitrile in 100 ml of dioxane is added and the mixture is refluxed for 5 hours. An additional 3 grams of sodium hydride suspension is added and the mixture refluxed for 17 hours. The mixture is then filtered, concentrated, and washed with petroleum ether to remove the mineral oil. The residual oil is then chromatographed on silica gel packed with chloroform and eluted with chloroform and chloroform containing increasing quantities of methanol. The fractions eluted with 0.5% and 1% methanol are combined and the solvent is evaporated to obtain 1H-benzimidazole-1-butanenitrile.

B. Preparation of 1H-benzimidazole-1-butanamine

A solution is prepared from 8.9 grams of the product of Preparation A and 150 ml of absolute ethanol, 0.8 grams of 10% palladium on charcoal and 8 ml of concentrated hydrochloric acid are added, and the resulting mixture is hydrogenated at room temperature and 50 PSI for 48 hours. The reaction mixture is then filtered, the solvent is evaporated from the filtrate, and the residue is treated with aqueous 2N sodium hydroxide solution and extracted with chloroform. The chloroform solution is dried and distilled to obtain 1H-benzimidazole-1-butanamine boiling at about 180°–186° C. at 1.2 mm pressure.

C. Preparation of N-[2-(3-benzyloxyphenyl)-2-hydroxyethyl]-1H-benzimidazole-1-butanamine A mixture of 6.75 grams of product of Preparation B, 7.37 grams of 3-benzyloxyphenylglyoxal hydrate and 2.16 grams of sodium borohydride in 100 ml of methanol is stirred at room temperature for 16 hours. The solvent is evaporated and the residue is mixed with 200 ml of chloroform and 100 ml of water. The chloroform layer is separated, washed several times with water and dried over magnesium sulfate. The solvent is then evaporated and the residue dried at 50° C. to obtain N-[2-(3-benzyloxyphenyl)-2-hydroxyethyl]-1H-benzimidazole-1-butanamine.

D. N-[2-hydroxy-2-(3-hydroxyphenyl)ethyl]-1H-benzimidazole-1-butanamine

The product of Preparation C (4.0 grams) is dissolved in 100 ml of glacial acetic acid, 1.0 gram of palladium on charcoal catalyst is added, and the mixture is hydrogenated at room temperature and a pressure of 50 pounds per square inch in a Parr apparatus for 16 hours. The resulting mixture is filtered to remove the catalyst and the acetic acid is evaporated from the filtrate. The residue is triturated with ether and then dissolved in about 50 ml of water. The aqueous solution is made basic (pH 9) with ammonium hydroxide and extracted twice with 1-butanol. The butanol extracts are combined, washed with water and dried over potassium carbonate and the solvent is evaporated to obtain a residue which is purified using column chromatography, e.g. a 75 gm. silica gel (63–200 mesh) column, packed with acetonitrile. The column is eluted with acetonitrile containing increasing quantities of conc. aq. ammonium hydroxide, e.g. 100 ml portions of 98:2, 96:4 and 92:8. Determination of purity of product is accomplished by T.L.C. The combined final fractions are evaporated in vacuo and dried to obtain N-[2-hydroxy-2-(3-hydroxyphenyl)ethyl]-1-H-benzimidazole-1-butanamine: mp=58°–62° C. (uncorr.); NMR (DMSO-$d_6$): $\delta$=1.06–2.04 (mult, 4, $CH_2$), 2.40–2.76 (mult, DMSO+$CH_2$); 4.10–4.41 (t,2, $NCH_2CH_2CH_2CH_2$—); 4.41–4.68 (t,1, CH(OH)—); 6.53–7.82 (mult, 8, arom); 8.25 (s,1, NCH=$\overline{N}$) ppm.

EXAMPLE 2

N-[2-hydroxy-2-(3-hydroxyphenyl)ethyl]-1H-benzimidazole-1-butanamine (1:1.5) oxalic acid salt 4.0 gm. of the product of Example 1, Preparation D, is dissolved in 80 ml of methanol with 1.55 gm. of oxalic acid. To the solution is added ether and the resultant solution is chilled overnight. The solids are filtered off and washed with ether and dried in vacuo to obtain the title compound: mp=162°-175° C.; NMR (DMSO-d$_6$): δ=1.50-2.14 (mult., 4, CH$_2$); 2.81-3.30 (mult., 4, CH$_2$); 4.12-4.45 (broad t, 2, —CH$_2$CH$_2$CH$_2$CH$_2$N); 4.68-5.0 (mult., 1); 6.59-7.82 (mult., 8, arom.); 8.32 (s,1, NCH=N) ppm.

FORMULATIONS

| FORMULATION 1 - TABLET OR CAPSULE - 30 mg. | |
|---|---|
| Ingredients | gm. |
| N—[2-hydroxy-2-(3-hydroxyphenyl)-ethyl]-1H—benzimidazole-1-butanamine | 30 |
| Lactose-Direct Tablet Grade | 150 |
| Avicel PH101 - (microcrystalline cellulose) | 20 |
| Corn Starch U.S.P. | 30 |
| Magnesium stearate | 2 |
| | 232 gm. |

Blend the N-[2-hydroxy-2-(3-hydroxyphenyl)ethyl]-1H-benzimidazole-1-butanamine and avicel PH101 in a P.K. blender using the intensifier low for 10 minutes. Mill the mixture through a #1 screen and return to the blender. To the blender now add the lactose and corn starch. Screen the magnesium stearate through a 40 mesh screen and add to the rest of the ingredients in the blender, blend for 15 minutes.

The blend is compressed into 1000 Tablets containing 30 mg of the active, or filled into 1000 hard gelating capsules containing 30 mg of the active.

| FORMULATION 2 - INJECTABLE 10 mg/10 ml AMPULE | |
|---|---|
| Ingredients | mg/ml |
| N—[2-hydroxy-2-(3-hydroxyphenyl)-ethyl]-1H—benzimidazole-1-butanamine dihydrochloride* | 1.0 mg. |
| 0.9 M Saline solution q.s. to | 1.0 ml. |

*Contains 0.82 mg of free base.

In a suitable container mix the ingredients until a clear solution is obtained. Buffer pH to 4-6 with NaOH if necessary. Filter the solution through a 0.45 micron millipore filter into a properly prepared receiving vessel. Fill into 10 ml #1 glass ampule. Flame seal the ampule and terminally sterilize at 120° C. for 20 minutes.

We claim:

1. A compound of the formula:

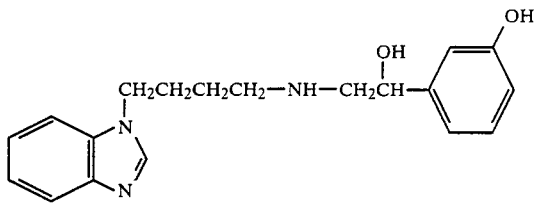

or a pharmaceutically acceptable acid addition salt thereof.

2. A compound of claim 1 which is N-[2-hydroxy-2-(3-hydroxyphenyl)ethyl]-1H-benzimidazole-1-butanamine.

3. A compound of claim 1 which is N-[2-hydroxy-2-(3-hydroxyphenyl)ethyl]-1H-benzimidazole-1-butanamine or a pharmaceutically acceptable acid addition salt thereof.

4. A pharmaceutical composition for producing a cardiotonic effect comprising a non-toxic cardiotonically effective amount of a compound of claim 1 in admixture with a non-toxic pharmaceutically acceptable carrier.

5. The method of eliciting a cardiotonic effect in a mammalian host having a disease condition in which therapeutic benefit is derived from elicitation of a cardiotonic effect, which comprises administering to said host a non-toxic cardiotonically effective amount of a compound of claim 1.

6. A method according to claim 5 wherein the host is an adult human being.

7. A method according to claim 6 wherein the host is suffering from congestive heart failure.

* * * * *